(12) United States Patent
Czabala (10) Patent No.: US 6,346,139 B1
(45) Date of Patent: Feb. 12, 2002

(54) TOTAL DELIVERY OXYGEN CONCENTRATION SYSTEM

(75) Inventor: Michael P. Czabala, Alpharetta, GA (US)

(73) Assignee: Respironics, Inc., Pittsburgh, PA (US)

( * ) Notice: Subject to any disclaimer, the term of this patent is extended or adjusted under 35 U.S.C. 154(b) by 0 days.

(21) Appl. No.: 09/560,754

(22) Filed: Apr. 28, 2000

Related U.S. Application Data (60) Provisional application No. 60/133,748, filed on May 12, 1999.

(51) Int. Cl.$^7$ .............................................. B01D 53/053
(52) U.S. Cl. ................................ 95/130; 95/96; 96/130; 96/144; 96/145; 55/356
(58) Field of Search .............................. 95/130; 96/115, 96/128, 130, 133, 144, 147; 55/356, 357

(56) References Cited

U.S. PATENT DOCUMENTS

| | | | | |
|---|---|---|---|---|
| 3,880,616 A | * | 4/1975 | Myers et al. ............... | 96/115 X |
| 4,302,224 A | * | 11/1981 | McCombs et al. .......... | 96/128 X |
| 4,331,455 A | * | 5/1982 | Sato .......................... | 95/130 X |
| 4,342,573 A | * | 8/1982 | McCombs et al. .......... | 96/128 X |
| 4,349,357 A | * | 9/1982 | Russell ...................... | 96/128 X |
| 4,378,982 A | * | 4/1983 | McCombs ................. | 96/130 X |
| 4,428,372 A | * | 1/1984 | Beysel et al. .............. | 96/130 X |
| 4,449,990 A | * | 5/1984 | Tedford, Jr. et al. ....... | 96/115 X |
| 4,502,873 A | * | 3/1985 | Mottram et al. ........... | 96/130 X |
| 4,545,790 A | * | 10/1985 | Miller et al. ............... | 96/130 X |
| 4,822,384 A | * | 4/1989 | Kato et al. ................. | 96/130 X |
| 4,867,766 A | * | 9/1989 | Campbell et al. .......... | 96/130 X |
| 4,880,443 A | * | 11/1989 | Miller et al. ............... | 96/115 X |
| 4,971,609 A | * | 11/1990 | Pawlos ........................ | 96/128 |
| 5,078,757 A | * | 1/1992 | Rottner et al. ............. | 96/130 X |
| 5,474,595 A | | 12/1995 | McCombs ...................... | 95/23 |
| 5,531,807 A | | 7/1996 | McCombs ...................... | 95/26 |
| 5,588,985 A | | 12/1996 | Shagott et al. ............... | 95/25 |
| 5,733,359 A | | 3/1998 | Doong et al. .................... | 95/8 |
| 5,906,672 A | * | 5/1999 | Michaels et al. ........... | 96/130 X |
| 5,997,617 A | * | 12/1999 | Czabala et al. ............. | 96/133 X |
| 6,190,441 B1 | * | 2/2001 | Czabala et al. ............. | 96/130 |

* cited by examiner

Primary Examiner—Robert H. Spitzer
(74) Attorney, Agent, or Firm—Michael W. Haas (57) ABSTRACT

A total delivery oxygen concentration system is provided to supply concentrated oxygen to end users having a variety of oxygen capacity requirements. The system includes a first oxygen concentrating device that may be operated either singularly to produce a first flow of concentrated oxygen or in conjunction with a supplemental oxygen concentrating device. When operating in conjunction with the supplemental oxygen concentrating device, the first oxygen concentrating device serves as a source of compressed air for the supplemental oxygen concentrating device and receives a second flow of concentrated oxygen from the supplemental oxygen concentrating device to provide a combined concentrated oxygen flow to the end user.

38 Claims, 7 Drawing Sheets

TOTAL DELIVERY OXYGEN CONCENTRATION SYSTEM

CROSS-REFERENCE TO RELATED APPLICATIONS

This application claims priority under 35 U.S.C. §119(e) from U.S. provisional patent application No. 60/133,748 filed May 12, 1999.

BACKGROUND OF THE INVENTION

1. Field of Invention

This invention relates generally to a total delivery system for supplying concentrated oxygen to a patient, and, more particularly, to a total delivery system including a portable oxygen concentrator for providing oxygen to ambulatory patients that can be interfaced with a stationary oxygen concentrator to provide additional oxygen capacity, power and sound dampening capability.

2. Description of the Related Art

Oxygen concentrators are frequently used as an unlimited source of oxygen for the treatment of patients who have had oxygen therapy prescribed by a physician, which is typically done to treat any of a variety of respiratory ailments and/or circulatory diseases. An oxygen concentrator typically uses a pressure swing absorption system to separate oxygen from the ambient air in the patient's environment. A typical oxygen concentrator can provide a flow of oxygen ranging from 1 liter per minute to about 5 liters per minute depending upon the condition and needs of the particular patient receiving the concentrated oxygen. In can be appreciated that the higher the patient's oxygen prescription, the more likely it is that the patient is bed-ridden or otherwise not ambulatory. Conversely, patients having relatively lower oxygen prescriptions, such as less than 3 liters per minute, are more likely to be ambulatory than a patient with a higher oxygen prescription.

The pressure swing absorption systems used in oxygen concentrators generally include molecular sieve beds for separating the gas mixture into an oxygen fraction and a nitrogen fraction. The oxygen fraction is provided to the patient while the nitrogen fraction is retained in the sieve bed and is subsequently purged. In a pressure swing absorption system, two sieve beds are utilized so that as one sieve bed separates nitrogen from the oxygen, the other sieve bed is simultaneously purged of the nitrogen absorbed during the prior separation cycle.

Typically, pressure swing absorption systems also include a compressor that draws air from the ambient environment and presents the air to the molecular sieves for separation of the gases. The type and size of compressor determines the overall oxygen flow rate capacity. Additionally, the compressor type and size are correlated to the level of noise produced by the system during operation. In general, large compressors required for providing higher rates of oxygen can be quite noisy, which may disturb the comfort of the patient and cause the patient to have difficulty sleeping while the compressor is operating.

Stationary oxygen concentrators have generally been used to supply oxygen to non-ambulatory patients or to ambulatory patients while they are resting or sleeping. Because stationary oxygen concentrators need not be moved, they can be constructed with large compressors and molecular sieves to provide a relatively high oxygen delivery capacity. Additionally, because stationary oxygen concentrators do not face size and weight constraints that are encountered when attempting to make a device portable, they can be constructed with substantial amounts of sound dampening insulation to muffle the compressor noise.

In contrast, portable oxygen concentrators have been developed to provide ambulatory patients with oxygen while they are traveling or moving about. It can be appreciated that it is desirable to keep the overall size and weight of a portable oxygen concentrator as small as possible, so that the concentrator may be easily transported. For this reason, portable oxygen concentrators generally have a relatively small oxygen delivery capacity, typically less than 3 liters per minute, which most likely suitable for ambulatory patients, i.e., patients with a relatively low oxygen prescription. While portable oxygen concentrators may include some sound dampening insulation, size and weight considerations generally dictate that they do not muffle compressor noise as efficiently as stationary oxygen concentrators.

As time passes, it is common for the condition of an ambulatory patient to worsen to the point where the patient requires additional oxygen capacity in excess of that supplied by a conventional portable oxygen concentrator. Typically, in these cases, the patient must then begin using a higher capacity stationary oxygen concentrator, incurring substantial costs and wasted resources in that the portable oxygen concentrator is no longer of use to such a patient. Similarly, ambulatory patients who need or desire the lower noise level of a stationary oxygen concentrator while sleeping, may also be required to obtain separate portable and stationary oxygen concentrators. The need for providing two concentrator systems to achieve the varied requirements, results in a higher cost to the patient or their insurer, health care provider, and/or reimbursement entity than would be encountered in buying either concentrator alone. Furthermore, durable medical goods suppliers must currently stock a number of both portable and stationary oxygen concentrators adequate to meet the demands of their clients, thereby incurring additional costs in maintaining their inventory.

SUMMARY OF THE INVENTION

Accordingly, it is an object of the present invention to provide a total delivery oxygen system that does not suffer from the disadvantages and/or shortcomings of conventional oxygen delivery systems.

It is a further object of the present invention to provide a total delivery oxygen system including a portable oxygen concentrator that can be combined with a low capacity stationary unit to provide additional oxygen capacity equivalent to that of a higher capacity stationary oxygen concentrator at a total cost substantially below that which would be required to provide a separate high capacity stationary oxygen concentrator.

The above objectives are accomplished according to the present invention by providing a total delivery oxygen concentration system having a first oxygen concentrating device that includes an air source for providing a flow of pressurized air derived from the ambient environment, a first primary molecular sieve for receiving the flow of pressurized air from the air source and for providing a first flow of oxygen enriched gas, a product tank disposed to receive the first flow of oxygen enriched gas from the first primary molecular sieve, and a valve for regulating the delivery of oxygen enriched gas from the first product tank to the end user. The total delivery oxygen concentration system also includes a supplemental oxygen concentrating device having a first supplemental molecular sieve for providing a second flow of oxygen enriched gas. In addition, a first pneumatic interface receives the second flow of oxygen enriched gas from the first supplemental molecular sieve and communicates the second flow of oxygen enriched gas to the product tank of the first oxygen concentrating device.

It is still another object of the present invention to provide a portable oxygen concentrator that can quickly and easily be docked with a base station, i.e., a supplemental oxygen concentrating device to provide augmented oxygen production. This object is achieved according to one embodiment of the present invention by providing a portable oxygen concentrating device capable of operating in conjunction with a supplemental oxygen concentrating device in a total delivery system. The portable oxygen concentrating device includes an air source and a first molecular sieve coupled to the air source to provide a first flow of oxygen enriched gas. In addition, a product tank is coupled to the first molecular sieve, and a first interface is coupled to the air source to provide pressurized air to a supplemental oxygen concentrating device. A second interface is coupled to the product tank to provide a second flow of oxygen enriched gas from the supplemental oxygen concentrating device to the product tank. In addition, a valve regulates the delivery of oxygen from the product tank to an end user.

It is yet another object of the present invention to provide a portable oxygen concentrator which can quickly and easily be docked with a base station for providing operational power or recharging the batteries of the portable concentrator as well as additional sound dampening insulation, or cooling capacity.

It is still another object of the present invention to provide a supplemental oxygen concentrating device capable of operating in conjunction with a first oxygen concentrating device in a total delivery system. According to a preferred embodiment of the present invention, the supplemental oxygen concentrating device includes a first molecular sieve that receives a first flow of pressurized air and provides a flow of oxygen enriched gas. In addition, a concentrated oxygen interface is coupled to the first molecular sieve that directs the flow of oxygen enriched gas from the first molecular sieve to a first oxygen concentrating device.

It is a further object of the present invention to provide a method providing oxygen enriched gas to a patient that does not suffer from the disadvantages of conventional oxygen concentration techniques. This object is achieved according to one object of the present invention by providing a method that includes providing a first oxygen concentrating device capable of outputting a first flow of concentrated oxygen, providing a supplemental oxygen concentrating device capable of outputting a second flow of concentrated oxygen, interfacing the first oxygen concentrating device with the supplemental oxygen concentrating device to combine the first and second flows of concentrated oxygen as a combined flow of concentrated oxygen. In addition, the method of the present invention includes directing this combined flow of concentrated oxygen to an end user, monitoring an inhalation state of the end user, and regulating the combined delivery of concentrated oxygen to the end user over a portion of the end user's breathing cycle.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
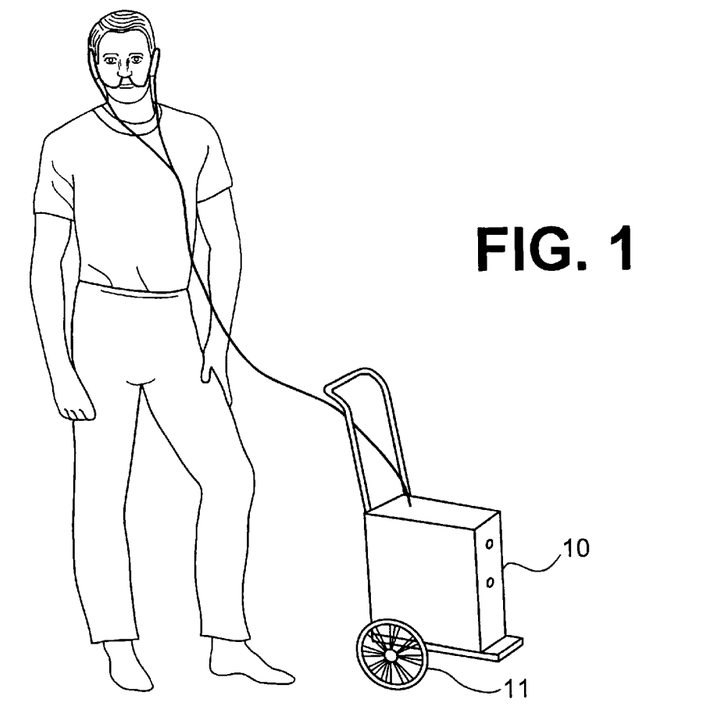
FIG. 1 is a perspective view of a portable oxygen concentrating device for use in a total delivery oxygen concentration system according to a presently preferred embodiment of the invention being used to treat a patient in ambulatory mode.
Figure 2:
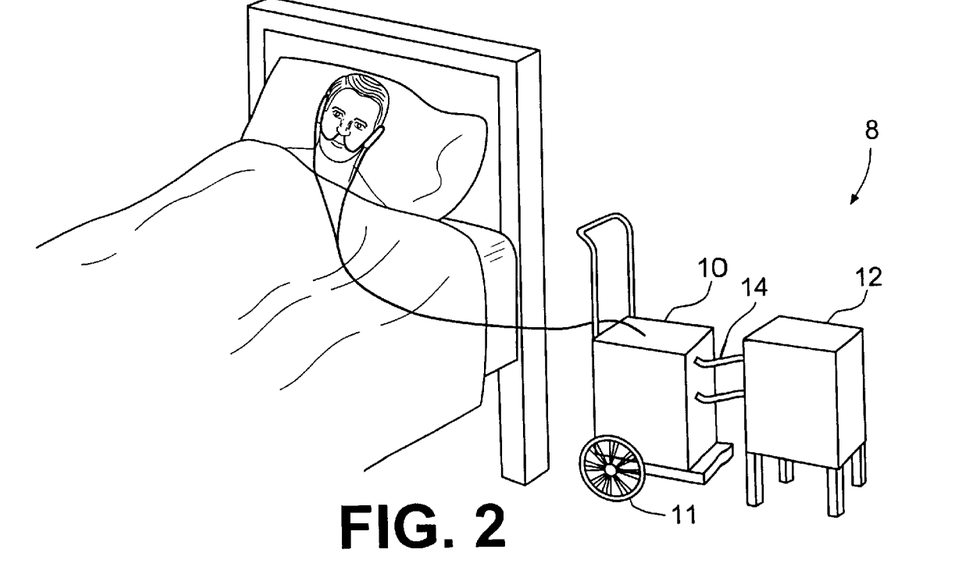
FIG. 2 is a perspective view of a total delivery oxygen concentration system according to a preferred embodiment of the present invention being used to treat a patient in a stationary mode.

As shown in FIGS. 1 and 2, a total delivery system 8 according to the principles of the present invention provides oxygen to a patient in either a lower capacity ambulatory mode or a higher capacity stationary mode. As shown in FIG. 1, when operating in an ambulatory mode, total delivery system 8 includes a portable oxygen concentrating device 10 that provides a patient with a flow of oxygen enriched gas derived from the ambient air in the patient's environment. The oxygen production capacity of portable oxygen concentrating device 10 is generally limited to the maximum anticipated oxygen requirement of an ambulatory patient to minimize the size and weight of portable oxygen concentrating device 10, thereby enhancing its portability.

Portable oxygen concentrating device 10 is shown in FIG. 1 as being transported on a wheel cart 11. It is to be understood, however, that a variety of techniques, for transporting the portable oxygen concentrating device can be used depending on the size and weight of the device. For example, a shoulder strap or carrying handle can be provided to transport the device.

As shown in FIG. 2, total delivery system 8 is also designed for operation in a stationary mode, utilizing both portable oxygen concentrating device 10 and a supplemental oxygen concentrating device 12. In this stationary or "docked" mode, the combination of portable oxygen concentrating device 10 and supplemental oxygen concentrating device 12, which interconnect to one another via an interface 14, supply a patient with a relatively high flow of oxygen enriched gas. The amount of oxygen supplied in this docked configuration is typically higher than the relatively lower levels of oxygen typically prescribed to an ambulatory patient that can be produced utilizing portable oxygen concentrating device 10 alone. The present invention also contemplates that supplemental oxygen concentrating device 12 provides additional cooling capacity, power, and/or sound insulation to enhance the operation of portable oxygen concentrating device 10 when operating in the stationary mode.

Figure 8:
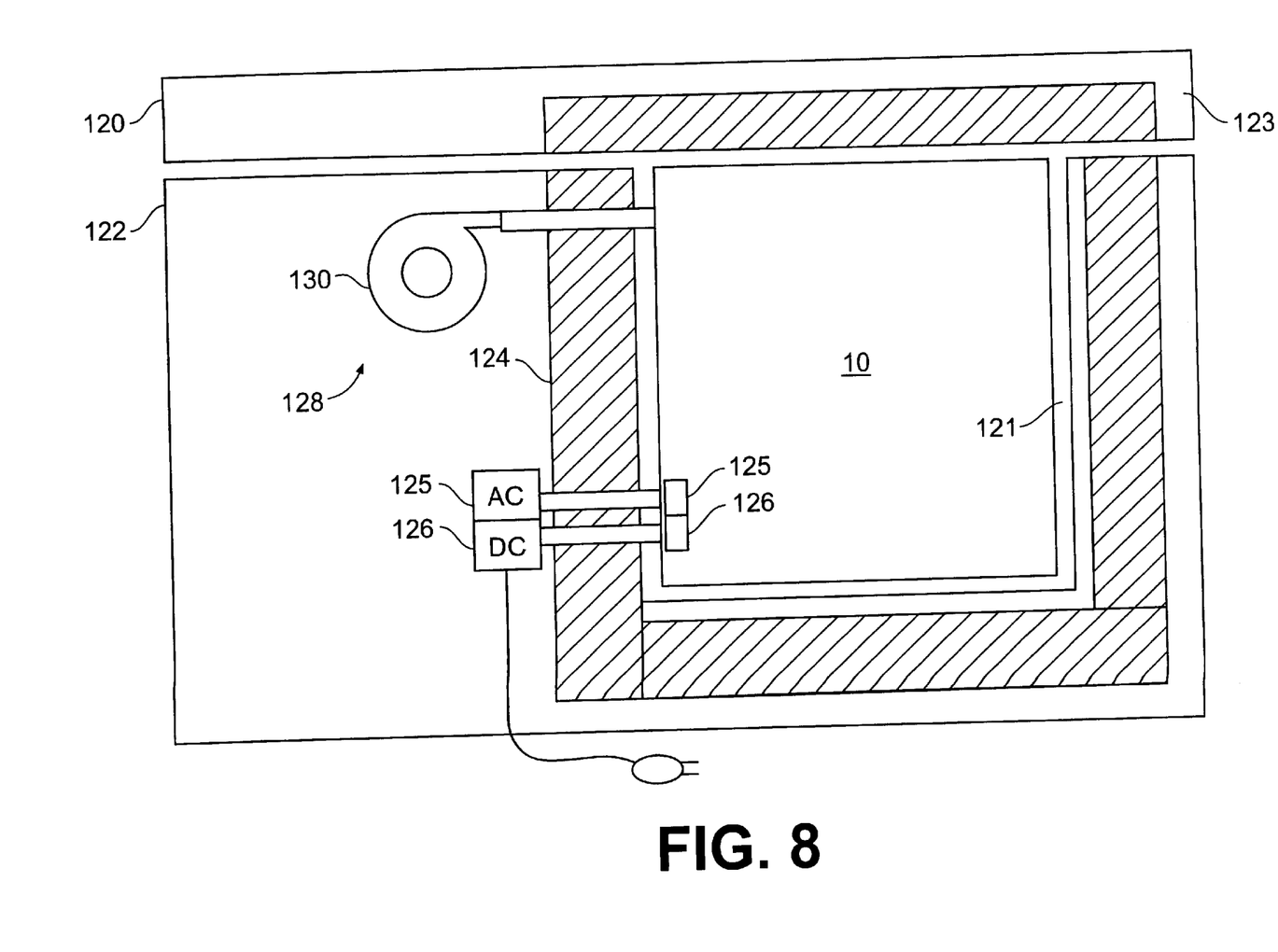
FIG. 8 is a block diagram illustrating a base station for providing a portable oxygen concentrator with additional functionality in accordance with yet another embodiment of the present invention.

In FIG. 2, portable oxygen concentrating device 10 and supplemental oxygen concentrating device 12 are illustrated as being separate, stand alone units that are interconnected for operating purposes via interface 14. It is to be understood, however, that the present invention contemplated connecting portable oxygen concentrating device 10 and supplemental oxygen concentrating device 12 using a variety of techniques, one variation of which is shown in FIG. 8 and described below with reference thereto. For example, supplemental oxygen concentrating device 12 can be configured as a docking port that receives a portion or all of the physical housing for portable oxygen concentrating device 10 much in the same way conventional computers can be docked into conventional docking stations.

Figure 3:
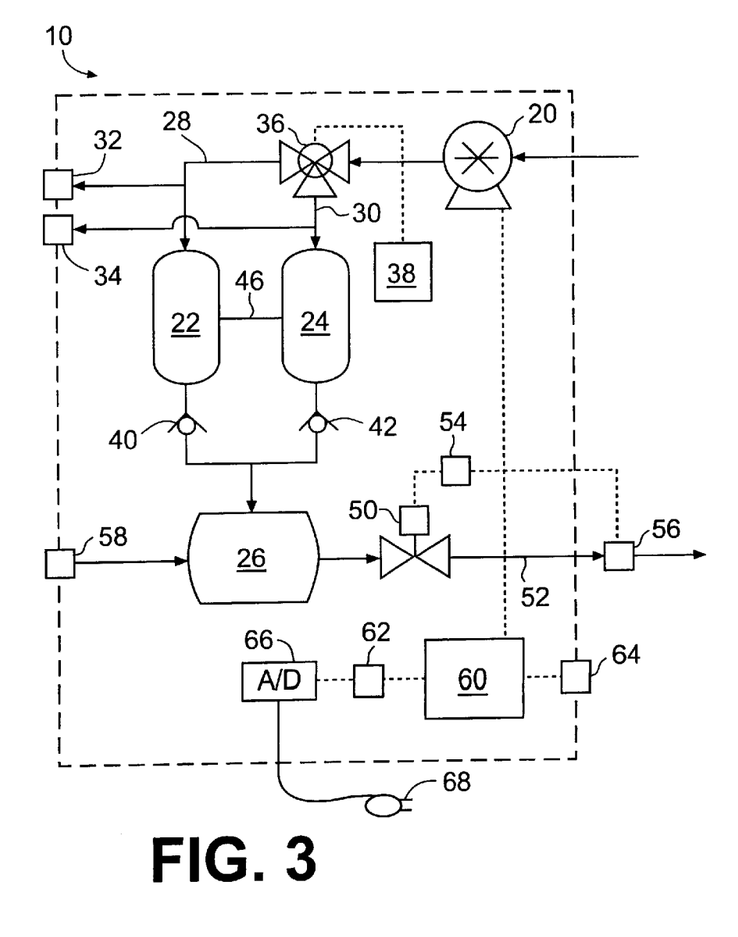
FIG. 3 is a schematic diagram illustrating the operational components and gas flow through a portable oxygen concentrating device in accordance with the embodiment of FIG. 1.
Figure 4:
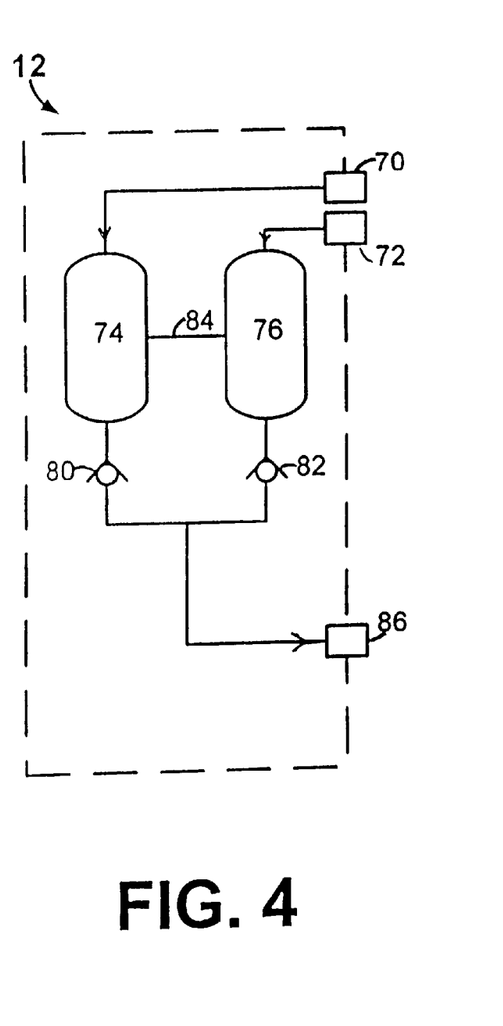
FIG. 4 is a schematic diagram illustrating the operational components and gas flow through a supplemental oxygen concentrating device in accordance with the embodiment of FIG. 2.
Figure 5:
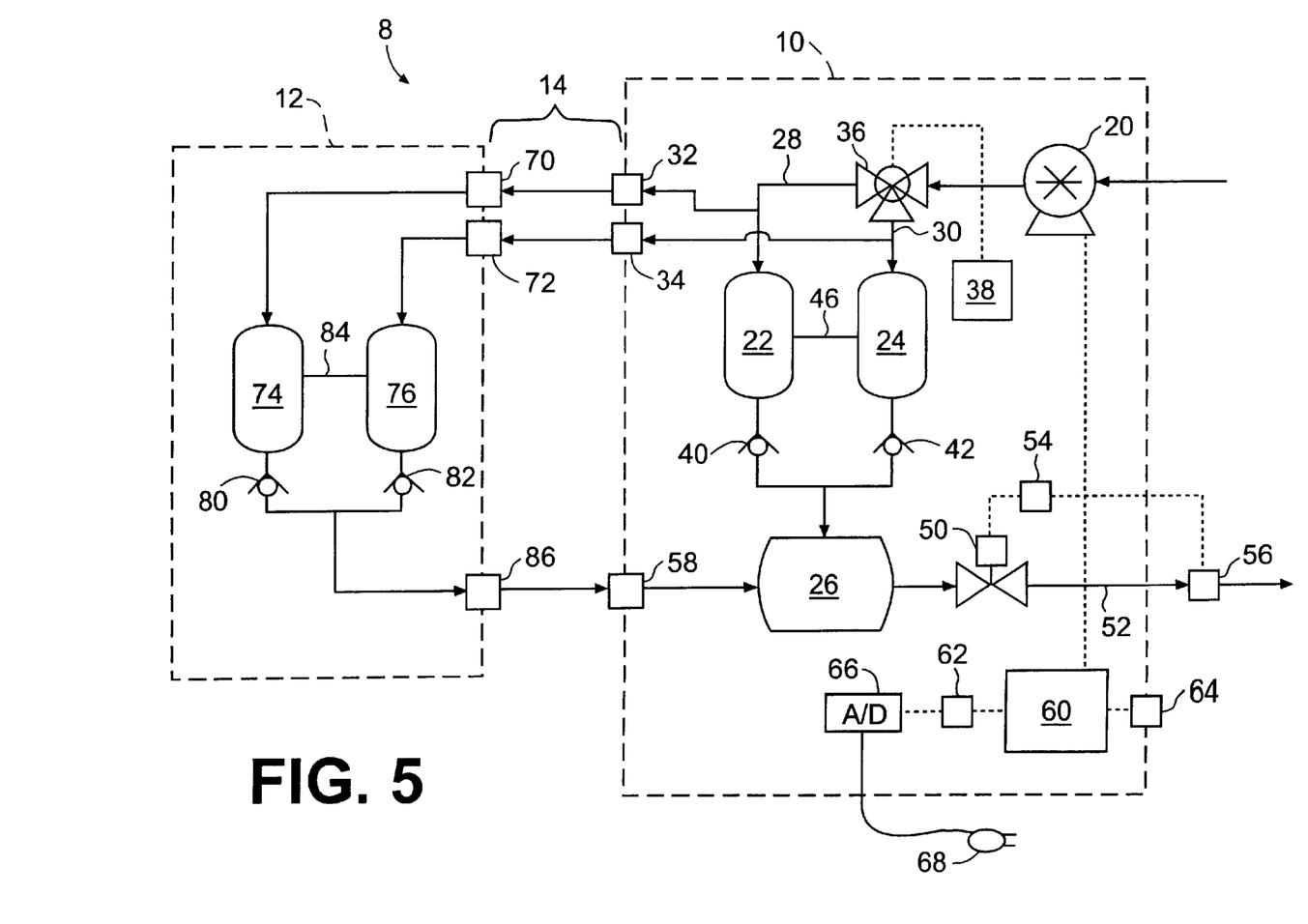
FIG. 5 is a schematic diagram illustrating the operational components and gas flow through a total delivery system operating in a stationary mode in accordance with the embodiment of FIG. 2.

FIGS. 3 and 4 illustrate schematic diagrams, respectively, of preferred embodiments of a portable oxygen concentrating device 10 and a supplementary oxygen concentrating device 12. FIG. 5 is a schematic diagram illustrating the operational components and a gas flow through a total delivery system 8 operating in stationary mode with portable oxygen concentrating device 10 and supplemental oxygen concentrating device 12 interconnected to provide a single flow of concentrated oxygen.

As shown in FIG. 3, portable oxygen concentrating device 10 is, in many respects, similar to a conventional pressure swing absorption (PSA) oxygen concentrating device, an example of which is found in U.S. Pat. No. 5,183,483, the contents of which are incorporated herein by reference. Portable oxygen concentrating device 10 includes a compressor 20 serving as a source of compressed air, a pair of molecular sieve canisters 22 and 24 for alternatively receiving the compressed air and retaining nitrogen, thereby enhancing the oxygen concentration of the compressed air, and a product tank 26 receiving the oxygen enriched gas produced by the sieve canisters. In addition to the components of a standard PSA oxygen concentrating device, portable oxygen concentrating device 10 includes sieve headers 28 and 30 and sieve interface couplings 32 and 34, whereby a portion of the pressurized air flow produced by compressor 20 may be diverted to supplemental oxygen concentrating device 12, and a concentrated oxygen coupling 58 for receiving a flow of oxygen enriched gas from such a supplemental oxygen concentrating device 12.

As shown in FIG. 3, as in a conventional PSA oxygen concentrating device, portable oxygen concentrating device 10 includes compressor 20, which is preferably a positive displacement compressor for providing a source of pressurized air. In the preferred embodiment, compressor 20 is a variable speed positive displacement compressor that produces a variable compressed air flow depending upon the speed at which it is operated. Compressor 20 is preferably a DC compressor operable on a DC power voltage commonly supplied by conventional rechargeable DC batteries, so that compressor 20 may serve as a portable compressed air source during operation in an ambulatory mode.

Also as shown in FIG. 3, portable oxygen concentrating device 10 includes a battery pack 60 for providing electrical power to compressor 20 when operating in an ambulatory mode to allow operation without requiring an external power source. Battery pack 60 preferably includes one or more rechargeable batteries. Portable oxygen concentrating device 10 preferably includes a DC battery charger 62, which is capable of recharging battery pack 60 while simultaneously providing operating power to compressor 20. DC external power coupling 64 is provided to receive DC power from an external source and to direct it to battery charger 62. Portable oxygen concentrating device 10 may also optionally include an AC/DC converter 66 for receiving AC power from an external source through AC external power coupling 68 and converting the AC power to DC power which may be directed to battery charger 62.

As shown in FIGS. 3 and 5, a first portion of pressurized air from compressor 20 is directed through a PSA control valve 36 to first and second sieve headers 28 and 30. PSA control valve 36 is preferably a standard control valve for a PSA system that alternatingly directs compressed air to either first sieve header 28 or second sieve header 30 in response to control signals received from a PSA controller 38. First sieve header 28 directs compressed air to first primary sieve canister 22 and to first sieve interface coupling 32. Likewise, second sieve header 30 directs compressed air to second primary sieve canister 24 and to second sieve interface coupling 34. First and second sieve interface couplings 32 and 34 are preferably standard quick connect couplings, for example, male couplings, which only allow passage of compressed air when connected to complementary couplings, such as female couplings, thereby ensuring that the couplings do not divert compressed air when operating in an ambulatory mode. It can be appreciated that one of ordinary skill in the art will recognize that a variety of other coupling mechanisms could also be used for couplings 32 and 34 as well as coupling 58.

As shown in FIGS. 3 and 5, portable oxygen concentrating device 10 differs from a conventional oxygen concentrating device in that a second portion of pressurized air from compressor 20 may be directed through sieve headers 28 and 30 to first and second sieve interface couplings 32 and 34 for delivery therethrough to supplemental oxygen concentrating device 12 when total delivery system 8 is operating in a stationary mode as shown, for example, in FIG. 5. This effectively allows sharing of the compressor 20 as an air source for both portable oxygen concentrating device 10 and supplemental oxygen concentrating device 12. As noted above, portable oxygen concentrating device 10 also includes concentrated oxygen coupling 58 for use in a stationary mode, which is adapted to receive a second flow of oxygen enriched gas from supplemental oxygen concentrating device 12 for delivery to product tank 26.

First and second primary sieve canisters 22 and 24 are standard molecular sieve canisters containing a nitrogen binding substrate, typically zeolite, through which an air flow is passed. In operation, PSA control valve 36 directs pressurized air to only one of first and second primary sieve canisters 22 and 24. The primary sieve canister 22 or 24 receiving the pressurized air flow operates in an oxygen concentrating mode while the remaining canister operates in a regenerating mode. In an operational mode, as the air flows through the nitrogen binding substrate of the respective primary sieve canister 22 or 24, a substantial portion of the atmospheric nitrogen is retained in the nitrogen binding substrate, thereby effectively enriching the oxygen concentration of the air flow to produce an oxygen enriched gas. This oxygen enriched gas flow is directed from the respective molecular sieve canister 22 or 24 through primary sieve outlet check valves 40 and 42, respectively, to prevent backflow of oxygen enriched gas into the primary sieve canisters 22 and 24. A regeneration line 46 is provided between first and second primary sieve canisters 22 and 24 to divert a portion of the oxygen enriched gas flow from the primary sieve canister currently in an operational mode to the primary sieve canister which is in a regeneration mode to trigger the release of bound nitrogen, thereby regenerating the nitrogen binding substrate.

Oxygen enriched gas produced by first and second primary molecular sieves 22 and 24 is directed to product tank 26, which serves as a reservoir of oxygen enriched gas for dispensing to the end user. In an exemplary embodiment of the present invention, oxygen enriched gas is released from product tank 26 through an oxygen conserving valve 50 to conduit 52, such as a nasal cannula, for delivery to the end user. Of course, other types of interface systems can be used to deliver the oxygen to the patient. Oxygen conserving valve 50 is preferably a solenoid valve that regulates the release of oxygen to the end user in response to control signals provided by an oxygen conserving device (OCD) controller 54.

In the illustrated exemplary embodiment, an inhalation sensor 56 is provided in communication with conduit 52 to detect a parameter correlated with the inhalation of the end user, such as temperature, flow and/or pressure. OCD controller 54 is responsive to signals from inhalation sensor 56 to provide control signals to regulate the release of oxygen enriched gas from product tank 26 to the end user only during the initial phase of inhalation during the end user's breathing cycle, thereby greatly enhancing the effectiveness of the flow of oxygen enriched gas. An example of an OCD flow control system suitable for use with the present invention is disclosed in U.S. Pat. Nos. 4,686,974 and 4,681,099, the contents of which are incorporated herein by reference. Such OCD systems are capable of meeting the requirements of a patient having a concentrated oxygen prescription of 3 liters per minute on as little as 0.75 liters per minute of compressed oxygen.

While the OCD system has been described above as detecting a parameter associated with the patient's respiratory cycle from the fluid characteristics within conduit 52, it is to be understood that the present invention contemplates using any sensor technique to differentiate between inspiration and expiration. For example, the present invention contemplates detecting the flow, pressure, or volume of fluids delivered to or inspired by the patient during breathing. Detecting these parameters associated with the patient's breathing can be accomplished, for example, using a pneumotach flow meter in communication with the patient's airway. The present invention also contemplates detecting sounds of the patient's breathing to discern when the patient breathing in and out so that oxygen enriched gas can be delivered only during inspiration.

In addition, the present invention contemplates detecting patient movement, such as the rise and fall of the chest, to detect the inspiratory and the expiratory phases of the respiratory cycle. Numerous techniques, such as resistance or inductance belts, pressure sensors, and impedance pneumography, are known for detecting such movement of the patient. Other suitable sensors that detect patient respiration include a temperature detecting system that detects temperature variations associated with a patient's respiration. For example, it is known to provide a thermister at or near the patient's airway to detect the heat associated with the expired air from the patient. Thus, when heat is detect by such a sensor, this indicates that the patient has reached the expiratory phase of the respiratory cycle. See, for example, U.S. Pat. Nos. 5,190,048 and 5,413,111 both to Wilkinson, the contents of which are incorporated herein by reference. In addition, a sensor can be provided to detect the electrical/neural activity of a patient associated with a patient's respiration, such as the EMG signal from the diaphragm to detect inspiration and expiration. Also, an oximeter can be used to detect respiration.

Use of the OCD to increase the efficiency of portable oxygen concentrating device 10 allows the overall size and weight of the various system components, most notably primary sieves 22 and 24, to be reduced, thereby enhancing the portability of portable oxygen concentrating device 10. It is estimated that the weight of the portable oxygen concentrating device may be reduced to as little as 12 pounds using the OCD technology. Additionally, portable oxygen concentrator 10 may be supported by wheels or casters to facilitate its portability for ambulatory but weak patients. It is to be understood, however, that the present invention contemplates that the OCD system can eliminated.

It is to be understood that the above-described oxygen conserving system, including oxygen conserving valve 50, OCD controller 54, and inhalation sensor 56, can be eliminated in favor of supplying a continuous flow of oxygen enriched gas to the user from product tank 26 regardless of whether the patient is in the inspiratory or expiratory phase of their respiratory cycle. Of course, other valves may be provided to control the flow of concentrated gas, for example, to prevent oxygen discharge when the system is turned off or otherwise inoperative.

The present invention also contemplates that the oxygen conserving system can be operated in either an oxygen conserving mode, as described above, where oxygen enriched gas in only delivered to the patient during inhalation, or in a continuous flow mode where oxygen is continuously delivered to the patient regardless of their respiratory cycle. This is accomplished, for example, by controlling valve 50 based on the mode selected by the patient. Of course, a patient interface device (not shown), such as a selector switch, must be provided to allow the user or caregiver to select the mode of oxygen delivery. OCD controller 54 operates valve 50 based on the mode selected by the user. If the continuous mode is selected, OCD controller 54 causes valve 50 to remain open throughout the patient's respiratory cycle. If the oxygen conserving mode is selected, OCD controller 54 causes valve 50 to allow oxygen enriched gas to be delivered to the patient only during inspiration, as discussed above.

As shown in FIGS. 4 and 5, supplemental oxygen concentrating device 12 includes first and second sieve interface couplings 70 and 72 adapted for connection to first and second sieve interface couplings 32 and 34 of portable oxygen concentrating device 10 to receive pressurized air produced by compressor 20 through sieve headers 28 and 30 respectively. Pressurized air received through first and second sieve interface couplings 70 and 72 is directed to first and second supplemental molecular sieve canisters 74 and 76, respectively. In an exemplary embodiment of the present invention, sieve interface couplings 32 and 34 are male couplings and couplings 70 and 72 are female couplings. Of course, one of ordinary skill in the art will recognize that one or both of the male and female couplings may also be easily reversed and that other interfacing mechanisms may be used within the scope of the present invention.

First and second supplemental sieve canisters 74 and 76 are also standard molecular sieve canisters, similar to primary sieve canisters 22 and 24. In a stationary mode of operation, PSA control valve 36 serves to alternatingly direct pressurized air through sieve headers 28 and 30 to supplemental sieve canisters 74 and 76 while simultaneously directing pressurized air to primary sieve canisters 22 and 24, respectively. Use of a single PSA control valve 36 ensures that supplemental sieve canisters 74 and 76 and primary sieve canisters 22 and 24 operate in synchronization with each other.

The supplemental sieve canister 74 or 76 receiving the pressurized air flow operates in an oxygen concentrating mode while the remaining canister operates in a regenerating mode. In an oxygen concentrating mode, nitrogen is removed as pressurized air flows through the nitrogen binding substrate of the respective supplemental sieve canister 74 or 76, thereby enriching the oxygen concentration of the air flow to produce an oxygen enriched gas. This oxygen enriched gas flow is directed from the respective molecular sieve canister 74 or 76 through supplemental sieve outlet check valves 80 and 82, respectively, to prevent backflow of oxygen enriched gas into the supplemental sieve canisters 74 and 76. A supplemental sieve regeneration line 84 is provided between first and second supplemental sieve canisters 74 and 76 to divert a portion of the oxygen enriched gas flow from the supplemental sieve canister currently in an operational mode to the supplemental sieve canister which is in a regeneration mode to trigger the release of bound nitrogen, thereby regenerating the nitrogen binding substrate.

Oxygen enriched gas flow from supplemental sieve canisters 74 and 76 is directed to concentrated oxygen coupling 86, which is adapted to connect to concentrated oxygen coupling 58 of portable oxygen concentrating device 10. Concentrated oxygen couplings 58 and 86 may be standard quick connect gas couplings which are closed when not engaged. When operating in a stationary mode, concentrated oxygen couplings 58 and 86 are engaged to direct oxygen enriched gas from supplemental sieve canisters 74 and 76 to product tank 26 of portable oxygen concentrating device 26.

Figure 6:
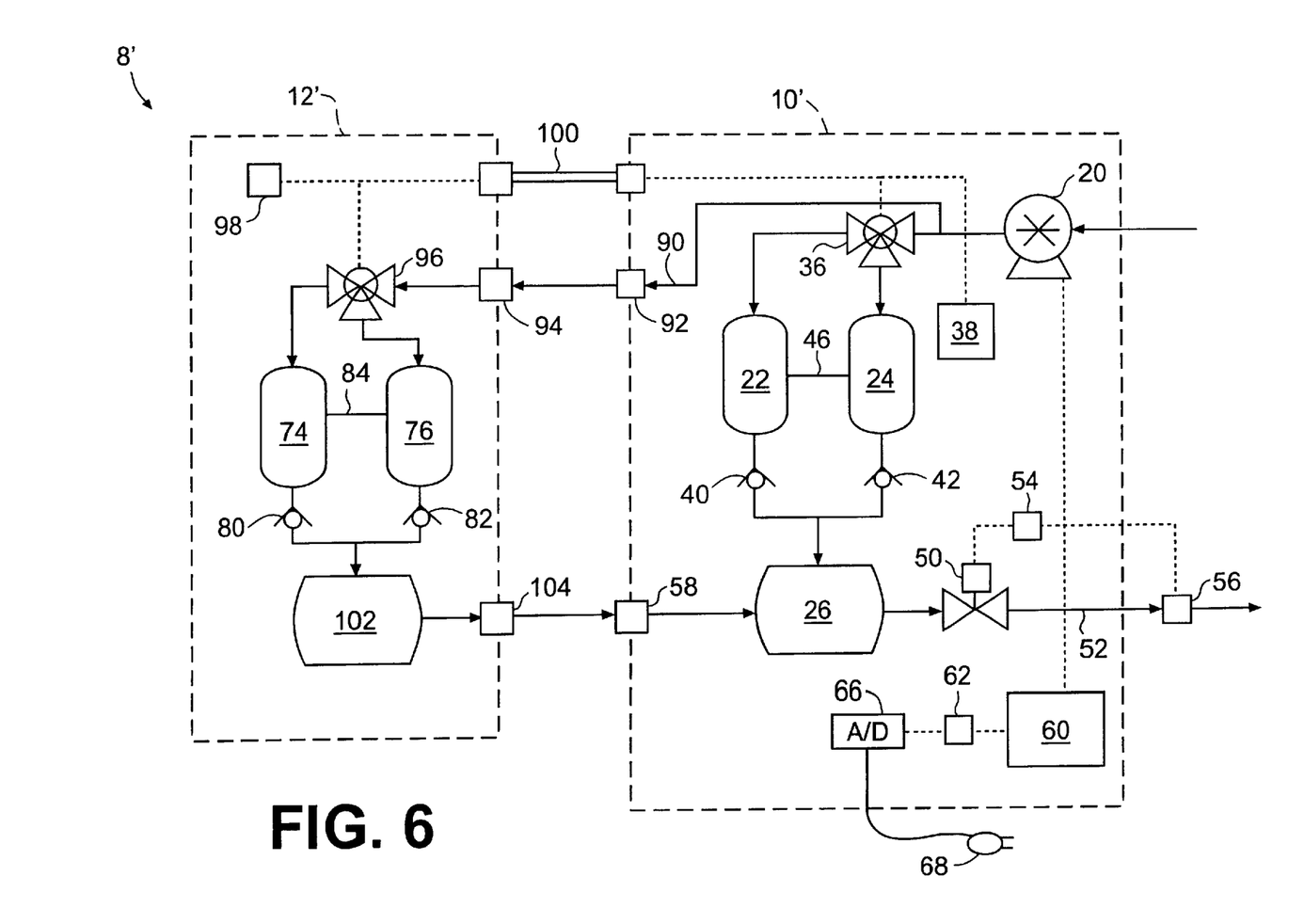
FIG. 6 is a schematic diagram illustrating an alternative embodiment of a total delivery system in accordance with the present invention.

FIG. 6 is a schematic diagram illustrating an alternative embodiment of a total delivery system 8' in accordance with the present invention. In the embodiment of FIG. 6, a portion of the pressurized air flow from compressor 20 is directed through a bypass line 90 to a pressurized air coupling 92 that is adapted for connection to a pressurized air coupling 94 on supplemental oxygen concentrating device 12'. The present invention contemplates that pressurized air couplings 92 and 94 are standard quick connect gas couplings that close when not engaged. When operating in a stationary mode, pressurized air couplings 58 and 86 are engaged to direct pressurized air from compressor 20, which thereby serves as an air source for supplemental oxygen concentrating device 12'.

In the embodiment of FIG. 6, supplemental oxygen concentrating device 12' also includes a supplemental PSA control valve 96 for alternatingly supplying pressurized air to supplemental sieve canisters 74 and 76. Supplemental PSA control valve 96 may either be responsive to control signals from a supplemental PSA controller 98 or, preferably, may be responsive to valve control signals received from primary PSA controller 38 through a control interface 100. Use of valve control signals from primary PSA controller 38 ensures that operation of supplemental PSA control valve 96 is synchronized with operation of primary PSA control valve 36.

As shown in FIG. 6, supplemental oxygen concentrating device 12' may also include a supplemental product tank 102 serving as a reservoir for oxygen enriched gas produced by air flow through supplemental sieve canisters 74 and 76. Oxygen enriched gas is directed from supplemental product tank 102 to concentrated oxygen coupling 104, which is adapted to interface with concentrated oxygen coupling 58 of portable oxygen concentrating device 10'. The present invention contemplates that concentrated oxygen couplings 58 and 104 are standard quick connect gas couplings that are closed when not engaged. When operating in a stationary mode, concentrated oxygen couplings 58 and 104 are engaged to direct oxygen enriched gas from supplemental product tank 102 to product tank 26 of portable oxygen concentrating device 10'. Accordingly, the flow of oxygen enriched gas to the patient from both product tank 26 and supplemental product tank 102 are subject to regulation by oxygen conserving valve 50 as previously discussed.

It is estimated that an effective oxygen flow equivalent to an oxygen prescription of 6 liters per minute can be achieved from a total oxygen flow of only 1.5 liters per minute using total delivery system 8 or 8' of FIGS. 5 and 6, respectively. Accordingly, it is estimated that primary sieve canisters 22 and 24 and supplemental sieve canisters 74 and 76 need only each support oxygen flows of approximately 0.75 liters per minute. This allows for a significant reduction of the size, cost and operational noise of oxygen concentrating devices 10, 10' and 12, 12' as compared to a standard 6 liter per minute PSA oxygen concentrating unit.

Figure 7:
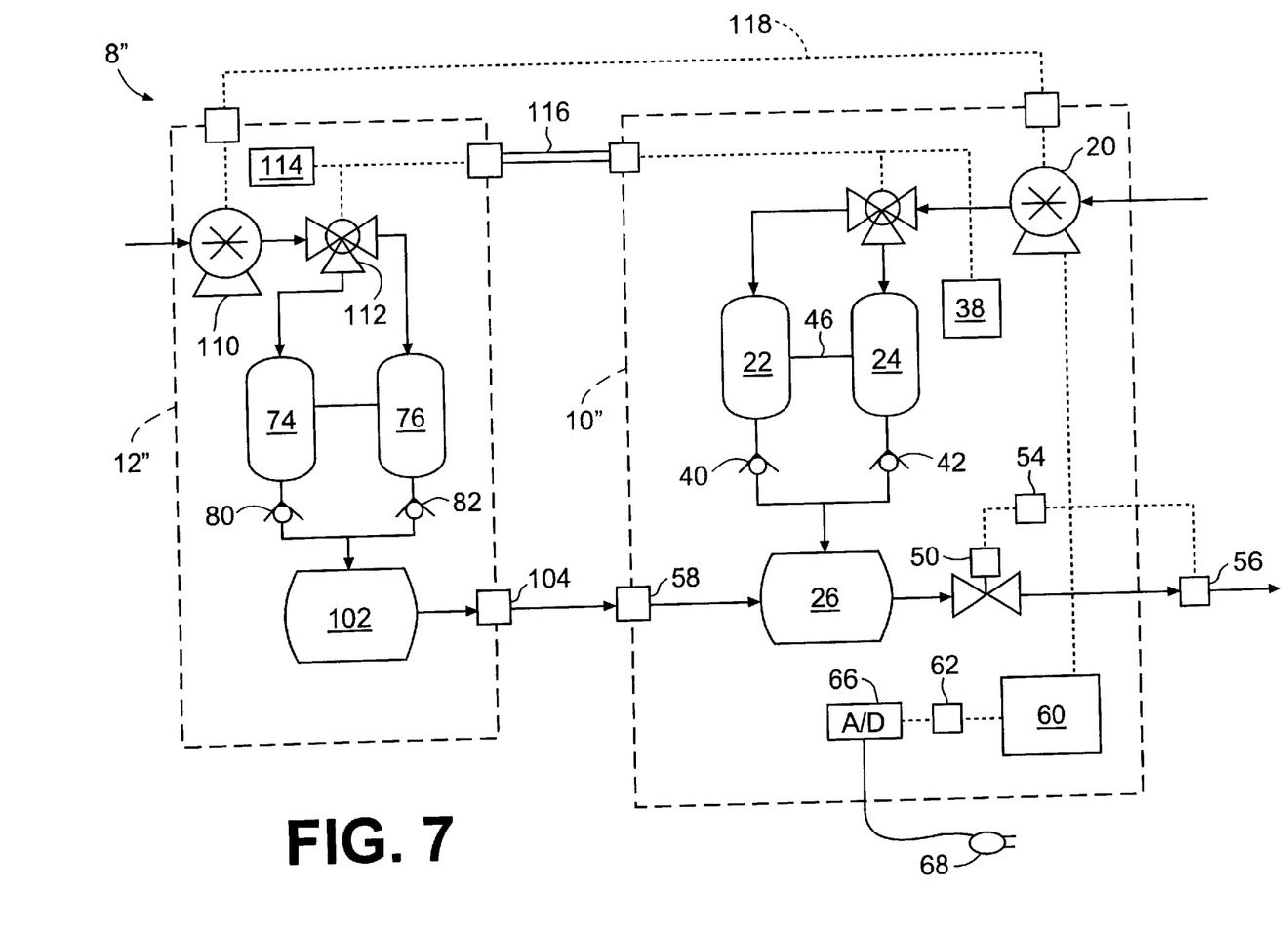
FIG. 7 is a schematic diagram illustrating yet another alternative embodiment of a total delivery system in accordance with the present invention.

FIG. 7 is a schematic diagram illustrating another alternative embodiment of a total delivery system 8" in accordance with the present invention. In the embodiment of FIG. 7, supplemental oxygen concentrating device 12" includes a second compressor 110, which serves as a supplemental air source for supplying pressurized air to supplemental sieve canisters 74 and 76. With the inclusion of second compressor 110, supplemental oxygen concentrating device 12" is functionally equivalent to a standard PSA oxygen concentrating device as previously described.

Supplemental oxygen concentrating device 12" also includes a supplemental PSA control valve 112 for alternatingly supplying pressurized air to supplemental sieve canisters 74 and 76. Supplemental PSA control valve 112 operates responsive to valve control signals from a supplemental PSA controller 114 or, preferably, is responsive to valve control signals received from primary PSA controller 38 through control interface 116. Use of valve control signals from primary PSA controller 38 ensures that operation of supplemental PSA control valve 112 is synchronized with operation of primary PSA control valve 36.

In the embodiment of FIG. 7, second compressor 110 is powered directly from an external power source, such as a conventional 110V AC outlet. Alternatively, second compressor 110 may also receive power from portable oxygen concentrating device 10" through a DC power coupling 118 only when portable oxygen concentrating device 10" is interfaced with supplemental oxygen concentrating device 12".

FIG. 8 is a block diagram illustrating a base station 120 for providing portable oxygen concentrator 10 with additional functionality in accordance with yet another embodiment of the present invention. In the embodiment of FIG. 8, base station 120 includes a housing 122 adapted to dockingly receive portable oxygen concentrating device 10. Housing 122 includes a chamber 121 defined therein and a cover member 123 that covers chamber 121 so that housing 122 substantially surrounds portable oxygen concentrating device 10 when docked in housing 122 as shown. Housing 120 includes sound dampener 124 that facilitates suppression of the operational noise of portable oxygen concentrating device 10 when it is docked within base station 120. In this embodiment, base station 120 serves effectively as a shell adding the additional functionality of sound dampening insulation to portable oxygen concentrating device 10 when portable oxygen concentrating device 10 is disposed within housing 122.

Also, as shown in FIG. 8, in a preferred embodiment, base station 120 includes an AC power coupling 125 and DC power coupling 126 for providing electrical power to portable oxygen concentrating device 10 as necessary for operation in a stationary mode and for recharging battery pack 60. The present invention also contemplates that base station 120 includes an auxiliary cooling unit 128 for providing additional cooling to the components of portable oxygen concentrating device 10, such as the compressor. Auxiliary cooling unit 128 preferably includes a cooling fan 130 for increasing the cooling air flow over the compressor or other components of portable oxygen concentrating device 10. It is to be understood that this base station assembly can be used with either of the portable oxygen concentrating devices discussed above.

Accordingly, when traveling, an ambulatory end user may utilize portable oxygen concentrating device 10, 10', 10" of total delivery oxygen concentrating system 8, 8', 8" in an ambulatory mode to supply an oxygen flow of up to 3 liters per minute, which should be sufficient to meet the oxygen needs of a majority of, if not all, ambulatory patients. In an ambulatory mode, portable oxygen concentrating device 10, 10', 10" operates self-sufficiently, relying on its battery pack 60 to provide power to its compressor 20 and control components. To conserve battery power, the end user may also connect portable oxygen concentrating unit 10 to an external DC power source, such as a car battery, using DC external power coupling 64 or to an external AC power source such as a wall outlet using AC external power coupling 68.

If, over time, the condition of the end user worsens and his or her oxygen needs increase beyond those typically required by an ambulatory patient, the end user may desire to enhance the oxygen capacity of portable oxygen concentrating device 10, 10', 10" by operating it in a stationary mode in conjunction with a supplemental oxygen concentrating device 12, 12', 12". Additionally, an ambulatory end user my wish to operate portable oxygen concentrating device 10, 10', 10" in a stationary mode in conjunction with supplemental oxygen concentrating device 12, 12', 12" in order to enjoy added functional benefits, such as enhanced sound dampening, enhanced cooling or battery recharging, which may have been omitted from portable oxygen concentrating device 10, 10', 10" for size and weight considerations.

Thus, it can be appreciated that an advantageous technique for providing oxygen enriched gas to a patient is provided according to the present invention. By utilizing a total delivery oxygen concentration system, the delivery of both a lower flow of oxygen for a typical ambulatory patient and a higher capacity oxygen flow for a typical non-ambulatory patient are accomplished. By providing a system wherein a lower capacity portable oxygen concentration device may be interfaced with a supplemental oxygen concentration device, patients having a wide range of oxygen requirements may be treated without incurring added costs of providing independent portable and stationary oxygen concentrating devices having a redundant capacity. Furthermore, by providing a portable oxygen concentrating device having an oxygen capacity sufficient for only the lower need ambulatory patient, the overall size and weight of the portable unit may be minimized, thereby enhancing its portability. Additionally, when resting or sleeping, the ambulatory end user may interface the portable oxygen concentrating device with a base station to provide the added functionality of a higher oxygen capacity, battery recharging, additional cooling or additional sound insulation, thereby also enjoying the benefits which would otherwise be sacrificed to enhance the portability of the portable oxygen concentrating device.

While the portable oxygen concentrating device and its companion supplemental oxygen concentrating device have been described above as each having a pair of molecular sieves, it is to be understood that one sieve can be utilized in one or both of these components. If one sieve is used in each, when the portable oxygen concentrating device and the supplemental oxygen concentrating device are combined, the present invention contemplates controlling the oxygen concentrating cycle, i.e., the charging, discharging and purging, of the two sieves as if they where in the same concentrator, such as sieves 22 and 24. It can thus be appreciated that an additional regeneration line will also be provided between such individual sieve canisters in the portable oxygen concentrating device and the supplemental oxygen concentrating device. The present invention also contemplates providing more than two sieves in one of both of the portable oxygen concentrating device and the supplemental oxygen concentrating device to increase oxygen output.

The above description of the present invention focuses on the use of pressure swing absorption to separate concentrated oxygen from air. It is to be understood, however, that the present invention contemplates using other techniques for gas fractionalization in place of the above-described pressure swing absorption system. For example, other types of gas fractionalization that are suitable for use with the oxygen concentration system of the present invention include cryogenic gas fractionalization, heated ceramic element gas fractionalization, and the use of hydrogen peroxide to produce concentrated oxygen.

It thus will be appreciated that the objects of this invention have been fully and effectively accomplished. Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A method for providing concentrated oxygen to an end user at a range of flow rates, the method comprising the steps of:

providing a first oxygen concentrating device capable of outputting a first flow of concentrated oxygen;

providing a supplemental oxygen concentrating device capable of outputting a second flow of concentrated oxygen;

interfacing the first oxygen concentrating device with the supplemental oxygen concentrating device to combine the first and the second flows of concentrated oxygen as a combined flow of concentrated oxygen; and directing the combined flow of concentrated oxygen to the end user.

2. A method according to claim 1, further comprising:
monitoring an inhalation state of the end user; and
regulating the combined flow of concentrated oxygen to the end user, in an oxygen conserving mode, over a portion of the end user's breathing cycle.

3. A method according to claim 1, further comprising:
switching between 1) the oxygen conserving mode in which the flow of oxygen enriched gas is delivered to the end user during a portion of the end user's breathing cycle and 2) a continuous delivery mode in which the flow of oxygen enriched gas is delivered to the end user throughout the end user's breathing cycle.

4. An oxygen concentration system for providing oxygen enriched gas to an end user comprising:
a first oxygen concentrating device comprising:
an air source that provides a first flow of pressurized air derived from ambient environment, the air source having a first pressurized air outlet,
a first primary molecular sieve operatively coupled to the air source to receive the first flow of pressurized air from the first pressurized air outlet, the first primary molecular sieve providing a first flow of oxygen enriched gas and having a first oxygen enriched gas outlet,
a product tank operatively coupled to the first primary molecular sieve to receive the first flow of oxygen enriched gas from the first oxygen enriched gas outlet, and
a valve operatively coupled to the product tank to regulate delivery of the oxygen enriched gas from the first product tank to an end user;
a supplemental oxygen concentrating device having a first supplemental molecular sieve for providing a second flow of oxygen enriched gas, the first supplemental molecular sieve having a second oxygen enriched gas outlet; and
a first pneumatic interface operatively coupled to the supplemental oxygen concentrating device so as to receive the second flow of oxygen enriched gas from the second oxygen enriched gas outlet and to communicate the second flow of oxygen enriched gas to the product tank.

5. An oxygen concentration system according to claim 4, wherein the air source generates a second flow of pressurized air and includes a second pressurized air outlet to direct the second flow of pressurized air, and further comprising a second pneumatic interface operatively coupled to the air source to receive the second flow of pressurized air from the second pressurized air outlet and to direct the second flow of pressurized air to the first supplemental molecular sieve.

6. An oxygen concentration system according to claim 5, wherein the supplemental oxygen concentrating device further comprises:
a second supplemental molecular sieve operatively coupled to the second pneumatic interface; and
a supplemental control valve operatively coupled between the second pneumatic interface and the first supplemental molecular sieve and between the second pneumatic interface and the second supplemental molecular sieve, wherein the supplemental control valve directs the second flow of pressurized air alternatively from the second pneumatic interface to the first and the second supplemental molecular sieves.

7. An oxygen concentration system according to claim 4, wherein the first oxygen concentrating device further comprises:

a second primary molecular sieve; and
a primary control valve operatively coupled to the first pressurized air outlet of the air source, the first primary molecular sieve, and the second primary molecular sieve, wherein the primary control valve directs the first flow of pressurized air alternatively to the first and the second primary molecular sieves, the primary control valve having a first primary control valve outlet that directs the first flow of pressurized air to the first primary molecular sieve and a second primary control valve outlet that directs the first flow of pressurized air to the second primary molecular sieve.

8. An oxygen concentration system according to claim 7, wherein the supplemental oxygen concentrating device further comprises a second supplemental molecular sieve, wherein the first oxygen concentrating device further comprises a first sieve header operatively coupled to the first primary control valve outlet and a second sieve header operatively coupled to the second primary control valve outlet, wherein the first sieve header communicates pressurized air simultaneously to the first primary molecular sieve and the first supplemental molecular sieve, and wherein the second sieve header communicates pressurized air simultaneously to the second primary molecular sieve and the second supplemental molecular sieve.

9. An oxygen concentration system according to claim 7, wherein the supplemental oxygen concentrating device further comprises:
a second supplemental molecular sieve operatively coupled to the second pneumatic interface; and
a supplemental control valve operatively coupled between the second pneumatic interface and the first supplemental molecular sieve and between the second pneumatic interface and the second supplemental molecular sieve, wherein the supplemental control valve directs the second flow of pressurized air alternatively from the second pneumatic interface to the first and the second supplemental molecular sieves.

10. An oxygen concentration system according to claim 9, further comprising a valve controller for controlling the primary control valve and the supplemental control valve in synchronization, wherein the primary control valve simultaneously directs pressurized air to the first primary molecular sieve while the supplemental control valve directs pressurized air to the first supplemental molecular sieve, and wherein the primary control valve simultaneously directs pressurized air to the second primary molecular sieve while the supplemental control valve directs pressurized air to the second supplemental molecular sieve.

11. An oxygen concentration system according to claim 4, wherein the supplemental oxygen concentrating device includes a second product tank operatively coupled to the first supplemental molecular sieve such that the second product tank receives the second flow of oxygen enriched gas from the second oxygen enriched gas outlet of the first supplemental molecular sieve.

12. An oxygen concentration system according to claim 4, wherein the supplemental oxygen concentrating device includes a power supply that provides electrical power to the first oxygen concentrating device and an electrical power coupling for coupling the electrical power to the first oxygen concentrating device.

13. An oxygen concentration system according to claim 4, wherein the supplemental oxygen concentrating device further comprises a supplemental air source for providing pressurized air to the first supplemental molecular sieve.

14. An oxygen concentration system according to claim 13, wherein the first oxygen concentrating device includes a power coupling adapted to provide electrical power to the supplemental air source.

15. An oxygen concentration system according to claim 4, wherein the supplemental oxygen concentrating device further comprises an auxiliary fan adapted to cool the first oxygen concentrating device responsive to the supplemental oxygen concentrating device being physically coupled to the first oxygen concentrating device.

16. An oxygen concentration system according to claim 4, wherein the supplemental oxygen concentrating device includes a housing adapted to receive the first oxygen concentrating device, wherein the housing includes a sound dampener adapted to reduce noise emitted by the first oxygen concentrating device.

17. An oxygen concentration system according to claim 4, wherein the first oxygen concentrating device further comprises an oxygen conserving device that includes:
   a sensor adapted to detect a parameter suitable for discerning an inhalation state of the end user, and
   a controller, responsive to an output of the sensor, that controls the valve in an oxygen conserving mode so as to restrict the flow of oxygen enriched gas from the product tank to the end user during a portion of the end user's breathing cycle.

18. An oxygen concentration system according to claim 17, further comprising an input device that allows switching of the oxygen concentration system between 1) the oxygen conserving mode in which the flow of oxygen enriched gas is delivered from the product tank to the end user during a portion of the end user's breathing cycle and 2) a continuous delivery mode in which the flow of oxygen enriched gas is delivered from the product tank to the end user throughout the end user's breathing cycle.

19. An oxygen concentration system for providing oxygen enriched gas to an end user comprising:
   a first oxygen concentration unit comprising:
      first oxygen concentration means for providing a first flow of oxygen enriched gas;
      a first product receiving means for receiving the first flow of oxygen enriched gas; and
      means for regulating the flow of oxygen enriched gas from the first product receiving means to an end user; and
   a supplemental oxygen concentration unit comprising:
      second oxygen concentration means for providing a second flow of oxygen enriched gas; and
      means for directing oxygen enriched gas from the second oxygen concentrating means to the first product receiving means.

20. An oxygen concentration system according to claim 19, wherein the means for regulating the flow of oxygen from the first product tank to the end user includes means, in an oxygen conserving mode, for restricting the flow of oxygen enriched gas from the first product receiving means to the end user during a portion of the end user's breathing cycle.

21. An oxygen concentration system according to claim 20, further comprising means for switching of the oxygen concentration system between 1) the oxygen conserving mode in which the flow of oxygen enriched gas is delivered from the product receiving means to the end user during a portion of the end user's breathing cycle and 2) a continuous delivery mode in which the flow of oxygen enriched gas is delivered from the product receiving means to the end user throughout the end user's breathing cycle.

22. A portable oxygen concentrating device capable of operating in conjunction with a supplemental oxygen concentrating device in a total delivery system, the portable oxygen concentrating device comprising:
   an air source adapted to provide a flow of pressurized air derived from ambient environment, the air source having a first outlet for providing a first flow of pressurized air and a second outlet for providing a second flow of pressurized air;
   a first molecular sieve operatively coupled to the first outlet and adapted to receive the first flow of pressurized air from the first outlet, the first molecular sieve providing a first flow of oxygen enriched gas;
   a product tank operatively coupled to the first molecular sieve, the product tank receiving the first flow of oxygen enriched gas from the first molecular sieve;
   a first interface operatively coupled to the product tank, the first interface being adapted to receive a second flow of oxygen enriched gas from the supplemental oxygen concentrating device and to direct the second flow of oxygen enriched gas to the product tank; and
   a valve operatively coupled to the product tank, the valve regulating a flow of oxygen from the product tank to an end user.

23. A portable oxygen concentrating device according to claim 22, further comprising:
   a second molecular sieve operatively coupled to the air source; and
   a control valve disposed between the first molecular sieve and the air source and between the second molecular sieve and the air source, the control valve directing the flow of pressurized air alternatively to the first and the second molecular sieves, the control valve having a first control valve outlet to direct the first flow of pressurized air to the first molecular sieve and a second control valve outlet to direct the first flow of pressurized air to the second molecular sieve.

24. A portable oxygen concentrating device according to claim 23, further comprising a valve controller operatively coupled to the control valve to control the control valve, the valve controller also providing an external valve control signal to the supplemental oxygen concentrating device.

25. A portable oxygen concentrating device according to claim 22, further comprising a power coupling adapted to receive electrical power from the supplemental oxygen concentrating device.

26. A portable oxygen concentrating device according to claim 22, further comprising a second interface operatively coupled to the second outlet, the second interface being adapted to direct the second flow of pressurized air from the second outlet to a supplemental oxygen concentrating device.

27. A supplemental oxygen concentrating device capable of operating in conjunction with a first oxygen concentrating device in a total delivery system, the supplemental oxygen concentrating device comprising:
   a first molecular sieve adapted to receive a first flow of pressurized air and to provide a flow of oxygen enriched gas; and
   a concentrated oxygen interface operatively coupled to the first molecular sieve, the concentrated oxygen interface being adapted to direct the flow of oxygen enriched gas from the first molecular sieve to the first oxygen concentrating device.

28. A supplemental oxygen concentrating device according to claim 27, further comprising a pressurized air interface adapted to receive the first flow of pressurized air from the first oxygen concentrating device and to direct the first flow of pressurized air to the first molecular sieve.

29. A supplemental oxygen concentrating device according to claim 27, further comprising:
- a second molecular sieve; and
- a control valve operatively coupled to the first and the second molecular sieve, wherein the control valve directs the first flow of pressurized air alternatively to the first and the second molecular sieves.

30. A supplemental oxygen concentrating device according to claim 29, further comprising a valve controller operatively coupled to the control valve, the valve controller controlling the control valve responsive to control signals received from the first oxygen concentrating device.

31. A supplemental oxygen concentrating device according to claim 27, further comprising a product tank operatively coupled to the first molecular sieve, the product tank receiving the flow of oxygen enriched gas from the first molecular sieve.

32. A supplemental oxygen concentrating device according to claim 27, further comprising a power coupling adapted to provide electrical power to a first oxygen concentrating device.

33. A supplemental oxygen concentrating device according to claim 27, further comprising a supplemental air source operatively coupled to the first molecular sieve, the supplemental air source providing the first flow of pressurized air to the first molecular sieve.

34. A supplemental oxygen concentrating device according to claim 27, further comprising an auxiliary fan adapted to cool the first oxygen concentrating device responsive to the first oxygen concentrating device being physically coupled to the supplemental oxygen concentrating device.

35. A supplemental oxygen concentrating device according to claim 27, further comprising a housing adapted to receive a first oxygen concentrating device, the housing including a sound dampener adapted to reduce operational noise of such first oxygen concentrating device responsive to the first oxygen concentrating device being physically coupled to the housing.

36. A stationary noise reducing housing adapted to muffle noise produced by a portable oxygen concentrating device during stationary use, the noise reducing housing comprising:
- a stationary housing adapted to receive the portable oxygen concentrating device; and
- a sound dampener disposed within the housing, the sound dampener reducing operational noise produced by the portable oxygen concentrating device responsive to the portable oxygen concentrating device being received within the stationary housing.

37. A stationary noise reducing housing according to claim 36, further comprising an auxiliary fan adapted to cool the portable oxygen concentrating device responsive to the portable oxygen concentrating device being received within the stationary housing.

38. A stationary noise reducing housing according to claim 36, further comprising a power coupling adapted to provide electrical power to the portable oxygen concentrating device responsive to the portable oxygen concentrating device being received within the stationary housing.

* * * * *